US009675763B2

(12) United States Patent
Huet

(10) Patent No.: US 9,675,763 B2
(45) Date of Patent: Jun. 13, 2017

(54) INJECTION ASSEMBLY

(71) Applicant: LABORATOIRE AGUETTANT, Lyons (FR)

(72) Inventor: Gildas Huet, Lyons (FR)

(73) Assignee: LABORATOIRE AGUETTANT, Lyons (FR)

( * ) Notice: Subject to any disclaimer, the term of this patent is extended or adjusted under 35 U.S.C. 154(b) by 0 days.

(21) Appl. No.: 14/410,411

(22) PCT Filed: Jun. 21, 2013

(86) PCT No.: PCT/FR2013/051455
§ 371 (c)(1),
(2) Date: Dec. 22, 2014

(87) PCT Pub. No.: WO2013/190249
PCT Pub. Date: Dec. 27, 2013

(65) Prior Publication Data
US 2015/0335826 A1 Nov. 26, 2015

(30) Foreign Application Priority Data

Jun. 22, 2012 (FR) ...................................... 12/55945

(51) Int. Cl.
*A61M 5/32* (2006.01)
*A61M 5/34* (2006.01)
(Continued)

(52) U.S. Cl.
CPC ........ *A61M 5/3202* (2013.01); *A61M 5/3213* (2013.01); *A61M 5/34* (2013.01);
(Continued)

(58) Field of Classification Search
CPC .... A61M 5/3202; A61M 5/3213; A61M 5/34; A61M 5/1626; A61M 5/3204;
(Continued)

(56) References Cited

U.S. PATENT DOCUMENTS 3,292,776 A * 12/1966 Penn ..................... A61M 5/002
206/366
4,720,285 A * 1/1988 Pickhard ............. A61M 5/3202
604/192
(Continued)

FOREIGN PATENT DOCUMENTS

EP 2462969 A1 6/2012
WO 0209797 A1 2/2002
WO 2009097634 A1 8/2009

OTHER PUBLICATIONS

International Search Report issued Oct. 1, 2013; re Application No. PCT/FR2013/051455; US 5 807 374 A, US 5 393 301 A, US 6 315 113 B1; EP 2 462 969 A1, WO 2009/097634 A1 and WO 02/09797 A1.

*Primary Examiner* — Bhisma Mehta
*Assistant Examiner* — Nilay Shah
(74) *Attorney, Agent, or Firm* — Cantor Colburn LLP

(57) ABSTRACT

The injection assembly (2) includes a prefilled injection device (3), such as a syringe, provided with a coupling tip (16), for example of the Luer-Lock type, and a protection device (4) comprising a protective portion (23) removably mounted on the coupling tip (16), a supporting portion (30) connected to the protective portion (23), and an injecting element (34) removably mounted on the supporting portion (30) in a storage position. The injecting element (34) comprising an injection needle (35) and a connecting tip (36) fluidly connected to the injection needle (35), the connecting tip (36) being adapted to be mounted on the coupling tip (16) of the injection device (3) in a position of use of the injecting element (34). The injecting element (34) and the supporting portion (30) are arranged in such a way that, in the position of storage of the injecting element (34), the connecting tip (36) is accessible to cooperate with the coupling tip (16).

12 Claims, 4 Drawing Sheets

(51) Int. Cl.
    *A61M 39/10* (2006.01)
    *A61M 5/162* (2006.01)
    *A61M 5/31* (2006.01)

(52) U.S. Cl.
    CPC ........... *A61M 5/1626* (2013.01); *A61M 5/321* (2013.01); *A61M 2005/3104* (2013.01); *A61M 2005/3107* (2013.01); *A61M 2039/1033* (2013.01); *A61M 2039/1094* (2013.01)

(58) Field of Classification Search
    CPC .... A61M 5/3205; A61M 5/321; A61M 5/343; A61M 5/50; A61M 5/002; A61M 2005/3103; A61M 2005/3215; A61M 25/0612; A61M 2005/3104; A61M 2005/3106; A61M 2005/3107; A61M 2005/311; Y10T 137/1767; Y10T 137/1692; F16K 17/16; F16K 17/40; F16K 17/403
    See application file for complete search history.

(56) References Cited

U.S. PATENT DOCUMENTS

| | | | |
|---|---|---|---|
| 5,393,301 A | | 2/1995 | Goldberg |
| 5,807,374 A | * | 9/1998 | Caizza .................. A61J 1/2096 141/27 |
| 6,068,614 A | * | 5/2000 | Kimber ................ A61M 5/178 264/478 |
| 6,315,113 B1 | | 11/2001 | Britton |
| 2005/0038391 A1 | * | 2/2005 | Wittland ................... A61L 2/20 604/192 |

\* cited by examiner

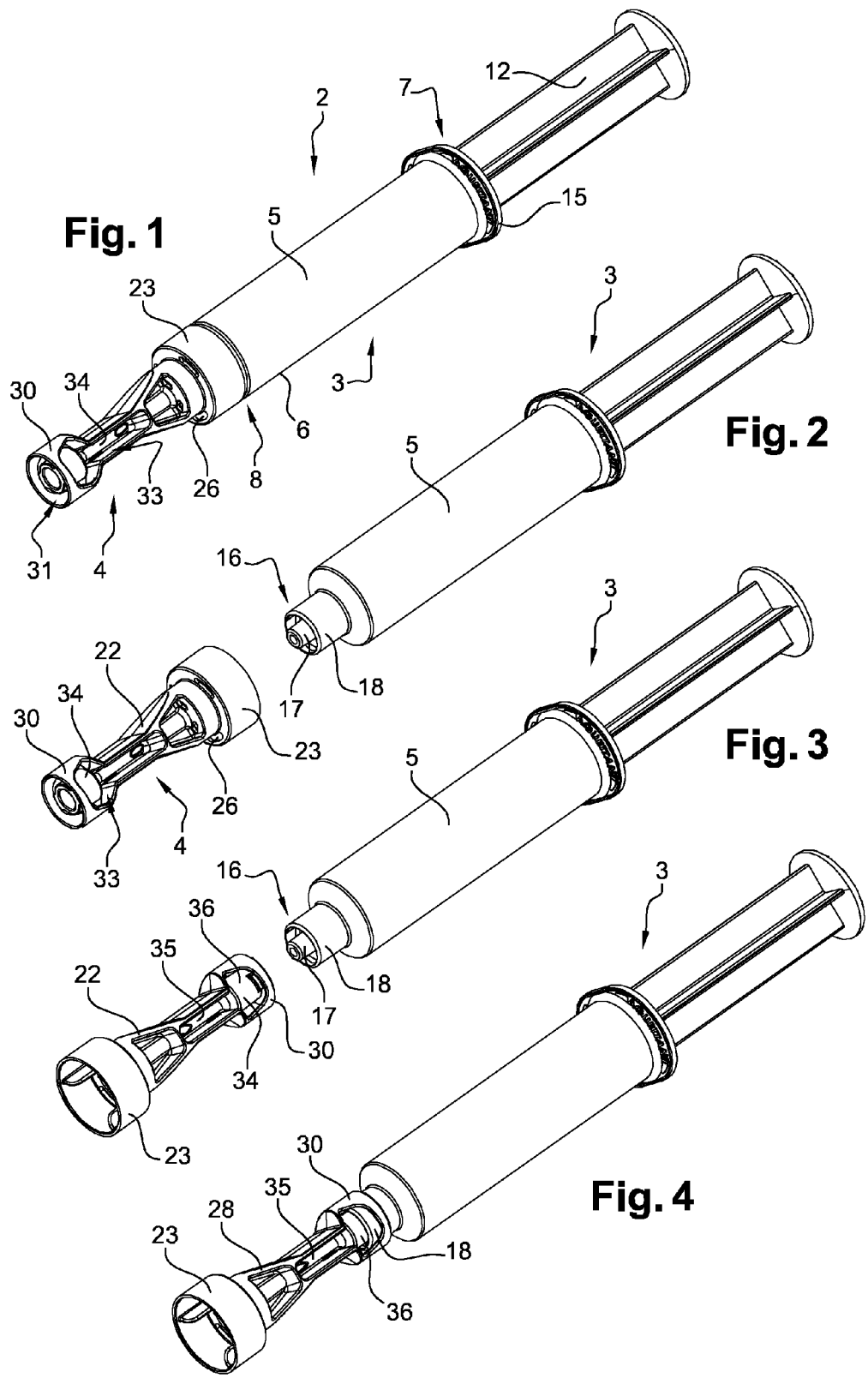

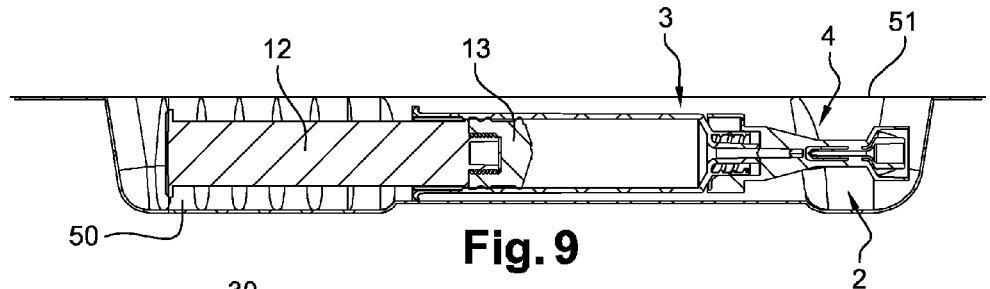
Fig. 9
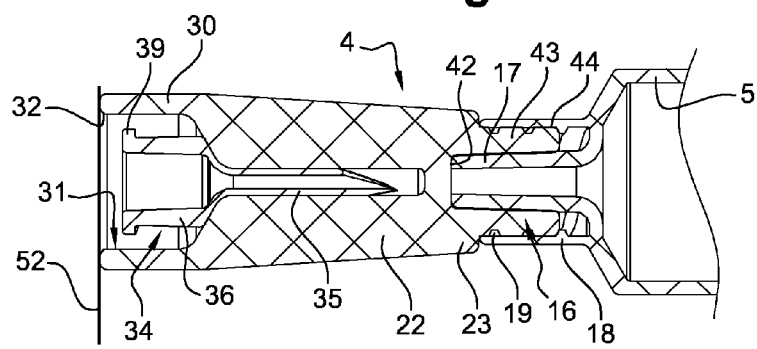
Fig. 10
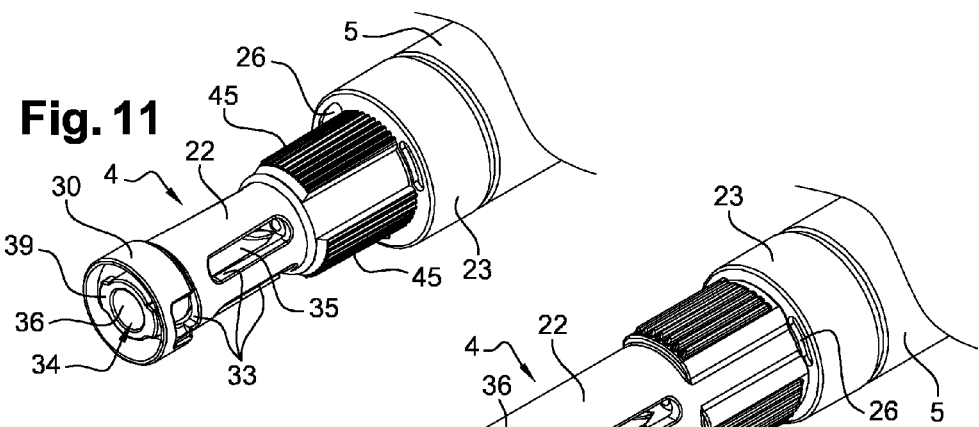
Fig. 11
Fig. 12
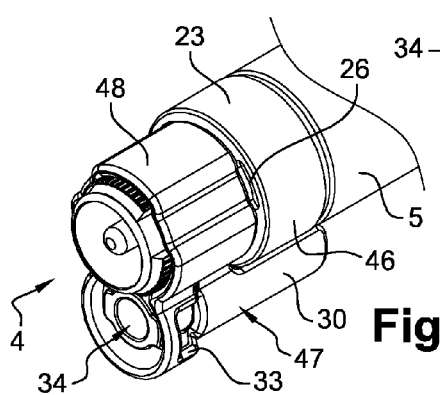
Fig. 13

INJECTION ASSEMBLY

TECHNICAL FIELD

The present invention concerns an injection assembly comprising in particular an injection device and a protection device.

BACKGROUND

An injection device, such as a prefilled syringe, includes, in a known manner, a coupling tip of the Luer or Luer-Lock type intended to cooperate with a tip having a complementary shape allowing to connect an injection needle or a perfusion line to the injection device. A coupling tip of the Luer type is generally composed of a truncated-cone tubular coupling part intended for the passage of a fluid, while a coupling tip of the Luer Lock type is further generally composed of a threaded locking sleeve coaxial with the coupling part and surrounding the latter.

In order to cover and protect the coupling part of the coupling tip, and optionally obturate said coupling part, a protective plug is usually screwed or fitted onto the coupling tip.

Therefore, when a user wishes to mount an injection needle on the injection device, for example in order to inject the content of the injection device in a container devoid of coupling tip complementary to that of the injection device, he must necessarily remove the protective plug from the injection device, open a conditioning in which an injection needle is disposed, take the injection needle and mount it on the coupling tip of the injection device.

Such a manipulation generates a significant number of gestures for the user and thereby multiplies the risks of contamination of the coupling tip of the injection device and/or the injection needle.

BRIEF SUMMARY

The present invention aims to overcome these drawbacks.

The technical problem underlying the invention comprises providing an injection assembly which is of a simple structure and inexpensive, and which allows to easily carry out the mounting of an injection needle on an injection device, while limiting the risks of contamination.

To this end, the present invention concerns an injection assembly, including:
a prefilled injection device comprising a coupling tip, the coupling tip including a tubular coupling part intended for the passage of a fluid, and
a protection device comprising:
  a protective portion removably mounted on the coupling tip of the injection device so as to cover and protect at least partially said coupling tip,
  a supporting portion connected to the protective portion, and
  an injecting element removably mounted on the supporting portion in a storage position, the injecting element comprising an injection needle and a connecting tip fluidly connected to the injection needle, the connecting tip being adapted to be mounted on the coupling tip of the injection device in a use position of the injecting element, the injecting element and the supporting portion being arranged in such a way that, in the storage position of the injecting element, the connecting tip is accessible to cooperate with the coupling tip.

The mounting of the injecting element directly on the protection device allows a user, when the protection device is mounted on the injection device, to carry out the mounting of the injection needle on this injection device simply by removing the protective portion of the injection device so as to release the coupling tip of the latter, and by cooperating the connecting tip of the injecting element with the coupling tip of the injection device.

Therefore, the injection assembly according to the invention allows mounting the injection needle on the injection device without changing hands and without the need to open another conditioning. This results in an easy mounting of the injection needle and a significant reduction of the risks of contamination of the coupling tip, and the fluid flowing through the latter.

Moreover, such a mounting of the injecting element on the protection device allows preserving the injection needle in a ready-to-use position, while maintaining it away from the fluid contained in the injection device. Such dispositions allow to avoid any problem of incompatibility between the injection needle and the fluid contained in the injection device during storage of the latter.

According to one embodiment of the invention, the injection device contains a liquid for medical use.

According to one embodiment of the invention, the injection device can be a syringe, a bag, a flexible tube, a flexible phial or flask, or a flexible vial.

According to one embodiment of the invention, the supporting portion is arranged to cover at least partially the injection needle and at least partially the connecting tip. Preferably, the supporting portion is arranged to cover at least partially the injection needle so as to prevent contact between the free end of the injection needle and the user's fingers.

Advantageously, the supporting portion includes a storage housing in which the injecting element is removably mounted.

According to one feature of the invention, the supporting portion includes at least one passage slot opening into the storage housing and intended for the passage of a sterilizing fluid. According to one embodiment of the invention, the supporting portion includes for example at least one passage slot opening into the storage housing at the injection needle and/or at least one passage slot opening into the storage housing at the connecting tip.

Preferably, the supporting portion includes a passage aperture opening into the storage housing, the passage aperture being arranged to allow removal of the injecting element from the storage housing.

The storage housing includes for example a first part into which the injection needle extends, and a second part forming a continuation of the first part and in which the connecting tip extends, the passage aperture opening into the second part of the storage housing.

According to one embodiment of the invention, the connecting tip is tubular and includes a first open end fluidly connected to the injection needle, and a second open end opposite to the first open end. According to this embodiment, the passage aperture is advantageously located facing the second open end of the connecting tip.

Advantageously, the supporting portion extends beyond the second open end of the connecting tip.

According to one embodiment of the invention, the injecting element is connected to the supporting portion via at least one breakable area.

According to another embodiment of the invention, the injecting element frictionally cooperates with at least one wall portion delimiting the storage housing.

According to one embodiment of the invention, the protection device includes a one-piece body comprising the protective and supporting portions. According to one embodiment of the invention, the one-piece body is flexible, and is for example made of elastomer.

According to one embodiment of the invention, the injecting element is monobloc, and can be for example metallic or made of plastic material.

According to one embodiment of the invention, the protection device comprises a cap including the protective portion, and a supporting member attached to the cap and including the supporting portion. The cap and the supporting member are for example made of plastic material.

The injecting element and the supporting portion are for example arranged in such a way that, in the storage position of the injecting element, the injection needle extends substantially parallel to the general direction of extension of the protection device.

According to one embodiment of the invention, the protective portion includes at least one passage orifice intended for the passage of a sterilizing fluid.

According to one embodiment of the invention, the injection assembly comprises obturating means arranged to obturate the free end of the coupling part of the coupling tip.

According to one embodiment of the invention, the protective portion comprises the obturating means or a coupling housing arranged to house at least partially the obturating means.

According to one embodiment of the invention, the obturating means include an obturating wall provided on the protective portion and arranged to obturate the free end of the coupling part of the coupling tip.

According to another embodiment of the invention, the obturating means include an obturator connected by a breakable area to the free end of the coupling part of the coupling tip. Advantageously, the protection device comprises a coupling portion arranged to cooperate with the obturator so that the rotation of the coupling portion about an axis of rotation parallel to the direction of extension of the coupling part drives in rotation the obturator so as to cause the rupture of the breakable area.

Preferably, the coupling portion includes a coupling housing in which the obturator is housed at least partially.

According to one embodiment of the invention, the coupling tip of the injection device is of the Luer or Luer Lock type. According to one embodiment of the invention, the coupling tip includes a threaded locking sleeve surrounding the coupling part.

According to one embodiment of the invention, the supporting portion and the connecting tip are arranged so as to delimit a passage space adapted for the passage of the locking sleeve of the coupling tip during the mounting of the injecting element on the coupling tip.

According to one embodiment of the invention, the protective portion includes a skirt arranged to be engaged on the outer wall of the locking sleeve of the coupling tip. Preferably, the passage orifice is arranged on the skirt of the protective portion. Advantageously, the skirt and the locking sleeve of the coupling tip delimit an internal chamber in which the passage orifice opens.

Advantageously, the coupling housing of the coupling portion opens into the inner volume delimited by the skirt of the protective portion.

According to another embodiment of the invention, the protective portion includes a mounting sleeve presenting an outer surface and an inner surface, the inner surface of the mounting sleeve being arranged to cooperate by shape complementarity with the outer surface of the coupling part of the coupling tip. The outer surface of the mounting sleeve includes for example a thread arranged to cooperate with the thread of the locking sleeve of the coupling tip.

According to another embodiment of the invention the skirt of the protective portion extends along at least half of the length of the locking sleeve.

According to one embodiment of the invention, the injection device is a prefilled syringe.

The prefilled syringe advantageously includes:

a tubular body comprising a first open end and a second end closed by a transverse wall provided with an flow orifice, the coupling tip being disposed at the second end of the tubular body and being fluidly connected to the flow orifice, a plunger extending through the aperture of the first end of the tubular body and including a piston slidably mounted in the tubular body, and an internal chamber delimited by the tubular body and the piston and containing a fluid.

Preferably, the obturator is molded in one single piece with the coupling tip and the tubular body.

Advantageously, the tubular body comprises a substantially cylindrical lateral wall. According to one embodiment of the invention, the skirt includes at least one portion, turned towards the tubular body, presenting, on at least one portion of its length, an outer diameter substantially identical to that of the lateral wall of the tubular body.

According to one embodiment of the invention, the injection assembly comprises a packaging, for example of the blister type, in which the injection device and the protection device are conditioned.

BRIEF DESCRIPTION OF THE DRAWINGS

In any case, the invention will be better understood using the following description with reference to the appended schematic drawing showing, by way of non-limiting examples, several embodiments of this injection assembly.

FIGS. 1 to 5 are perspective views of an injection assembly according to a first embodiment of the invention in various positions of use.

FIG. 9 is a longitudinal sectional view of the injection assembly of FIG. 1 conditioned in a packaging.

FIG. 10 is a partial longitudinal sectional view of an injection assembly according to a second embodiment of the invention.

FIGS. 11 to 13 are partial perspective views of an injection assembly according to respectively a third, a fourth and a fifth embodiments of the invention.

DETAILED DESCRIPTION

Figure 5:
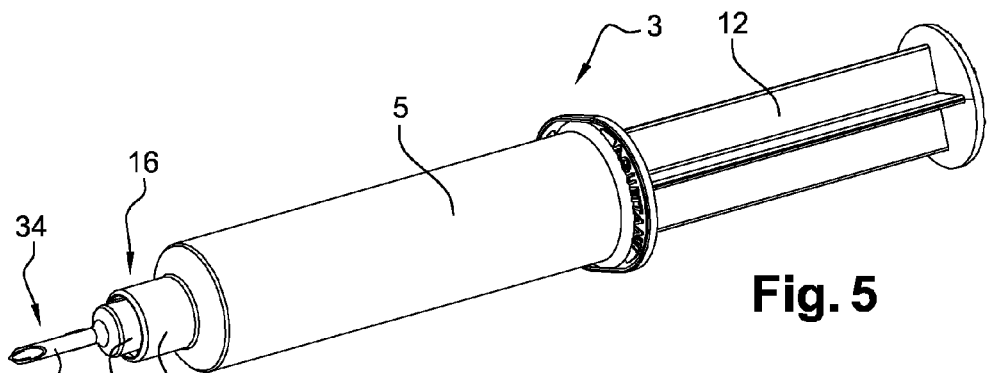

FIG. 1 shows an injection assembly 2 according to a first embodiment of the invention, which comprises an injection device 3 and a protection device 4 mounted on the injection device 3.

According to this first embodiment of the invention, the injection device 3 is formed by a prefilled syringe and comprises a tubular body 5 including a substantially cylindrical lateral wall 6. The lateral wall 6 presents a first open end 7 and a second end 8 closed by a transverse wall 9 provided at its center with a flow orifice 11. The injection device 3 also comprises a rod 12 forming a plunger which extends through the aperture of the first end 7 of the lateral wall 6. The rod 12 includes, at its end located inside the tubular body 5, a piston 13 slidably mounted inside the tubular body 5 along the longitudinal axis thereof. The tubular body 5 and the piston 13 therefore define an internal chamber 14 filled with a fluid which may be for example a drug solution, a solvent, etc.

The outer surface of the tubular body 5 includes a bearing flange 15 at the first end 7 on which the user's fingers press when a thrust is exerted by the latter on the end of the rod 12 opposite to the one connected to the piston 13.

The injection device 3 further comprises a coupling tip 16 of the Luer lock type disposed at the second end 8 of the lateral wall 6 of the tubular body 5, on the outer face of the transverse wall 9. The coupling tip 16 comprises a tubular coupling part 17 communicating with the flow orifice 11 of the transverse wall 9, and a locking sleeve 18 disposed coaxially with the coupling part 17 and surrounding the latter. The coupling part 17 is advantageously truncated-cone shaped, the aperture located to the side of the largest diameter of the coupling part 17 coinciding with the flow orifice 11. The locking sleeve 18 preferably includes a thread 19 arranged on its inner wall.

The injection device 3 includes moreover an obturator 20 connected by a breakable area 21 to the free end of the coupling part 17. The tubular body 5, the coupling tip 16 and the obturator 20 are for example made of synthetic material and in one single piece by molding.

The breakable area 21 between the coupling part 17 and the obturator 20 is advantageously carried out by an annular thinning of the material along the connecting line between the free end of the coupling part 17 and the obturator 20. Such a configuration of the breakable area 21 allows easy separation of the obturator 20 and the coupling part 17.

Figure 6:
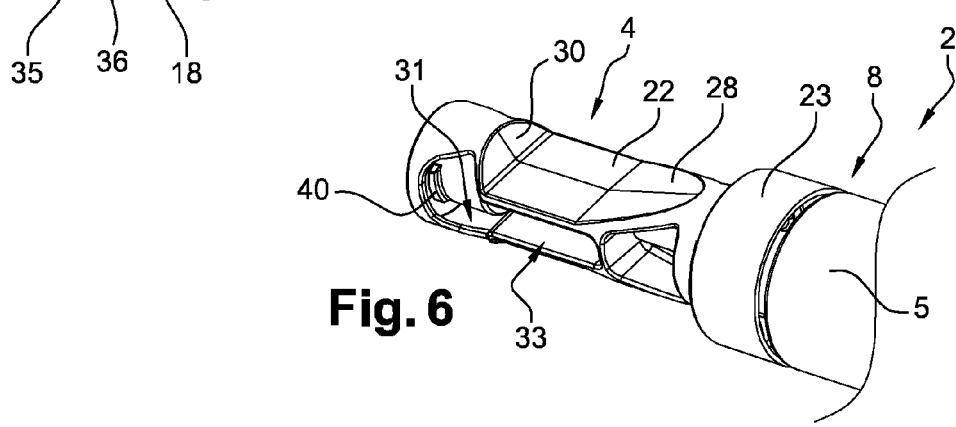
FIG. 6 is a partial perspective view, on an enlarged scale, of the injection assembly of FIG. 1.
Figure 7:
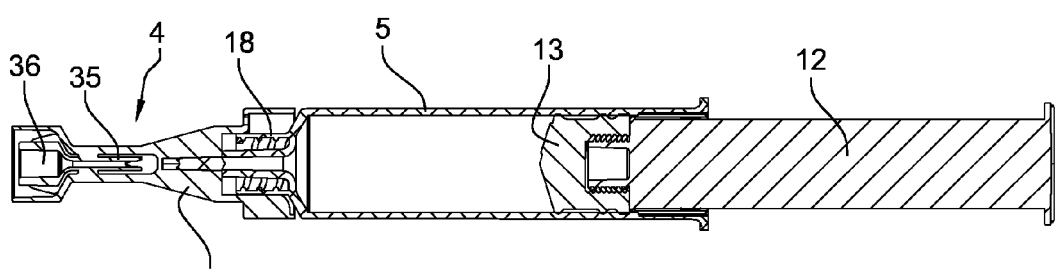
FIG. 7 is a longitudinal sectional view of the injection assembly of FIG. 1.
Figure 8:
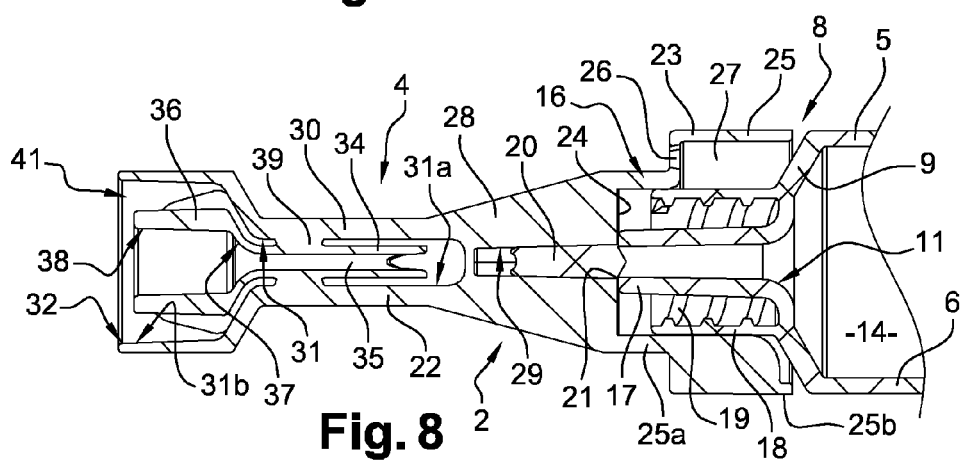
FIG. 8 is a partial longitudinal sectional view, on an enlarged scale, of the injection assembly of FIG. 1.

According to the embodiment shown in FIGS. 6 and 7, the protection device 4 comprises a one-piece body 22 comprising a protective portion 23 adapted to be removably mounted on the coupling tip 16 of the injection device 3 so as to preserve the sterility of the coupling tip 16.

The protective portion 23 comprises a transverse wall 24 from which protrudes a skirt 25 arranged to engage on the outer wall of the locking sleeve 18. The skirt 25 is arranged to extend beyond the end of the locking sleeve 18 turned towards the tubular body 5 of the injection device 3, and to extend preferably until the vicinity of the tubular body 5 of injection device 3.

The skirt 25 comprises a first cylindrical part 25a, and a second part 25b extending from the first part 25a. The second part 25b is turned towards the tubular body 5 of the injection device 3, and presents an outer diameter substantially identical to that of the lateral wall 6 of the tubular body 5.

The protective portion 23 comprises moreover at least one passage orifice 26 intended for the passage of a sterilizing fluid. The passage orifice 26 is for example arranged in the second part 25b of the skirt 25. The skirt 25 and the locking sleeve 18 are arranged to delimit at least one internal chamber 27 in which the passage orifice 26 opens. Therefore, during wet heat sterilization of the injection assembly 2, the steam may arrive from outside the protection device 4 towards the areas to be sterilized of the coupling tip 16. Of course, the skirt 25 might include several passage orifices 26 each opening into an internal chamber 27.

The one-piece body 22 also comprises a coupling portion 28 integral with the protective portion 23 and extending from the latter. The coupling portion 28 includes a coupling housing 29 opening into the transverse wall 24 and into the inner volume delimited by the skirt 25. The coupling housing 29 is preferably centered on the longitudinal axis of the skirt 25.

As shown in FIG. 7, the coupling housing 29 is arranged to cooperate with the obturator 20 so that the rotation of the coupling portion 28 about an axis of rotation coincident with the axis of the coupling part 17 drives in rotation the obturator 20 so as to cause rupture of the breakable area 21.

According to the embodiment shown in FIG. 7, the obturator 20 and the coupling housing 29 each have a conical shape. This feature allows press-fitting of the obturator 20 in the coupling housing 29 so that, after rupture of the breakable area 21, the obturator 20 is maintained in the coupling housing 29 and cannot fall to the ground. According to another embodiment, the obturator 20 and the coupling housing 29 might present complementary polygonal shapes, for example hexagonal shapes.

The one-piece body 22 of the protection device 4 also comprises a supporting portion 30 integral with the coupling portion 28 and extending from the latter. The supporting portion 30 comprises a storage housing 31 including a first housing part 31a turned towards the coupling portion 28, and a second housing part 31b forming a continuation of the first housing part 31a. The supporting portion 30 also comprises a passage aperture 32 opening into the storage housing 31, and more particularly in the second housing part 31b.

The supporting portion 30 comprises two passage slots 33 diametrically opposite and each opening into the storage housing 31. Each passage slot 33 is intended for the passage of a sterilizing fluid, and advantageously opens into the first and second housing parts 31a, 31b.

The protection device 4 further comprises an injecting element 34, preferably monobloc, removably mounted in the storage housing 31 of the supporting portion 30 in a storage position. The injecting element 34 can be for example metallic or made of plastic material.

The injecting element comprises an injection needle 35 and a connecting tip 36 fluidly connected to the injection needle. The connecting tip 36 is tubular and includes a first open end 37 fluidly connected to the injection needle 35, and a second open end 38 opposite to the first end 37.

The injection needle 35 extends into the first housing part 31a, and the connecting tip 36 extends into the second housing part 31b in such a way that the second end 38 of the connecting tip 36 is located facing the passage aperture 32. It should of course be noted that the passage aperture 32 is arranged to allow removal of the injecting element 34 from the storage housing 31. Advantageously, the free end of the supporting portion 30 extends beyond the second end 38 of the connecting tip 36.

According to the embodiment shown in FIGS. 6 and 7, the injecting element 34 is connected to the supporting portion 30 via at least two breakable areas 39, and is molded in one single piece with the one-piece body 22. The breakable areas 39 are more particularly arranged to join the connecting tip 36 to the supporting portion 30.

The connecting tip 36 is adapted to be mounted on the coupling tip 16 of the injection device 3 in a position of use of the injecting element 34. Indeed, the connecting tip 36 comprises two fastening lugs 40 arranged on its outer wall and arranged to cooperate with the thread 19 of the locking sleeve 18 of the coupling tip 16. In addition, the inner wall of the connecting tip 36 is arranged to cooperate by shape complementarity with the outer wall of the coupling part 17 of the coupling tip 16.

The supporting portion 30 and the connecting tip 36 are arranged to delimit a substantially annular passage space 41 adapted for the passage of the locking sleeve 18 of the coupling tip 16 in order to allow the mounting of the injecting element 34 on the coupling tip 16.

Under conditions of storage of the injection assembly 2, the injection device 3 equipped with the protection device 4 are advantageously conditioned in a blister 50 which can be closed for example by a cap 51 made of peeling paper.

The method for coupling the injecting element 34 on the injection device 3 will now be described with reference more particularly to FIGS. 1 to 5.

The coupling method comprises the following steps:
removing the injection assembly 2 from the blister in which it is conditioned,
driving in rotation the protection device 4 around its longitudinal axis so as to sever the breakable area 21 between the obturator 20 and the coupling part 17,
removing the protection device 4 so as to release the coupling tip 16 (see FIG. 2)
returning the protection device 4 in such a way that the connecting tip 36 is turned towards the coupling tip 16 (see FIG. 3),
screwing the connecting tip 36 of the injecting element 34 on the coupling tip 16 by making the fastening lugs 40 of the connecting tip 36 cooperate with the thread 19 of the locking sleeve 18 (see FIG. 4), and this until the breakable areas 39 joining the injecting element 34 to the supporting portion 30 are severed,
removing the one-piece body 22 from the coupling tip 16, the injecting element 34 remaining on the injection device 3 due to the cooperation between the connecting tip 36 and the coupling tip 16 (see FIG. 5).

FIG. 10 shows an injection assembly 2 according to a second embodiment of the invention which differs from that shown in FIGS. 1 to 8 mainly in that the injection device 3 is devoid of obturator and in that the protective portion 23 presents an obturating wall 42 arranged to obturate the free end of the coupling part 17 of the coupling tip 16. The one-piece body 22 is advantageously made of elastomer.

In addition, according to this second embodiment, the protective portion 23 includes a mounting sleeve 43 presenting an outer surface and an inner surface. The outer surface of the mounting sleeve 43 includes a thread 44 arranged to cooperate with the thread 19 of the locking sleeve 18 of the coupling tip 16, while the inner surface of the mounting sleeve 43 is arranged to cooperate by shape complementarity with the outer surface of the coupling part 17 of the coupling tip 16.

Furthermore, according to this second embodiment, the injecting element 34 frictionally cooperates with a wall portion delimiting the storage housing 31.

According to an alternative embodiment, the passage aperture 32 can be obturated by a cap 52 intended to preserve the sterility of the injecting element 34. Such a cap must be removed by the user before mounting the injecting element on the coupling tip 16 in order to preserve the sterility of the latter.

FIGS. 11 and 12 represent an injection assembly 2 according to a third and a fourth embodiments which differ from that shown in FIGS. 1 to 8 mainly in that the protection device 4 presents ribs 45 disposed on the outer face of the one-piece body 22 in order to promote its setting in rotation. The ribs 45 are for example arranged on the coupling portion 28 of the protection device 4.

According to these third and fourth embodiments, each passage slot 33 opens either into the first housing part 31a or into the second housing part 31b.

FIG. 13 represents an injection assembly 2 according to a fifth embodiment of the invention which differs from that shown in FIGS. 1 to 8 mainly in that the protection device 4 comprises a cap 46 including the protective and coupling portions 23, 28, and a supporting member 47 attached on the cap 46 and including the supporting portion 30 in which the injecting element 34 is mounted. The supporting member 47 advantageously comprises a mounting portion 48, for example an annular portion, integral with the supporting portion 30 and mounted on the coupling portion 28. According to this fifth embodiment, the injection assembly 34 is offset with respect to the longitudinal axis of the coupling tip 16.

Figure 14:
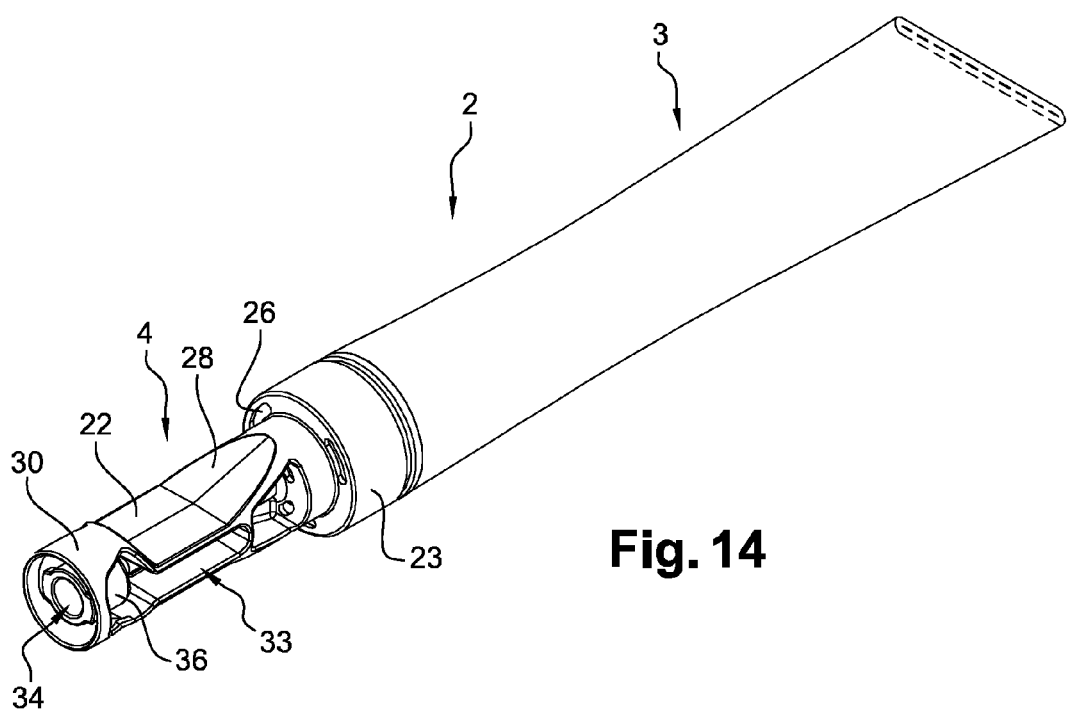
FIG. 14 is a perspective view of an injection assembly according to a sixth embodiment of the invention.

FIG. 14 represents an injection assembly 2 according to a sixth embodiment of the invention which differs from that represented in FIGS. 1 to 8 essentially in that the injection device 3 is a flexible injection tube.

It goes without saying that the invention is not limited to the sole embodiments of this injection assembly, described above by way of examples, it encompasses on the contrary all the alternative embodiments.

The invention claimed is:
1. An injection assembly, including:
a prefilled injection device comprising a coupling tip, the coupling tip including a tubular coupling part intended for a passage of a fluid,
an obturator obturating a free end of the tubular coupling part of the coupling tip, the obturator being connected by a breakable area to the free end of the tubular coupling part, and
a protection device comprising:
a one-piece body including:
a protective portion removably mounted on the coupling tip of the injection device so as to cover and protect at least partially said coupling tip,
a coupling portion connected to the protective portion and including a coupling housing configured to cooperate with the obturator, and
a supporting portion connected to the coupling portion, and
an injecting element removably mounted on the supporting portion in a storage position, the injecting element comprising an injection needle and a connecting tip fluidly connected to the injection needle, the connecting tip being adapted to be mounted on the coupling tip of the injection device in a position of use of the injecting element, the injecting element and the supporting portion being arranged in such a way that, in the storage position of the injecting element, the connecting tip is accessible to cooperate with the coupling tip.

2. The injection assembly according to claim 1, wherein the supporting portion is arranged to cover at least partially the injection needle and at least partially the connecting tip.

3. The injection assembly according to claim 1, wherein the supporting portion includes a storage housing in which the injecting element is removably mounted.

4. The injection assembly according to claim 3, wherein the supporting portion includes at least one passage slot opening into the storage housing and intended for a passage of a sterilizing fluid.

5. The injection assembly according to claim 3, wherein the supporting portion includes a passage aperture opening into the storage housing, the passage aperture being arranged to allow a removal of the injecting element from the storage housing.

6. The injection assembly according to claim 5, wherein the storage housing includes a first part in which the injection needle extends, and a second part forming a continuation of the first part and in which the connecting tip extends, the passage aperture opening into the second part of the storage housing.

7. The injection assembly according to claim 1, wherein the connecting tip is tubular and includes a first open end fluidly connected to the injection needle, and a second open end opposite to the first open end.

8. The injection assembly according to claim 7, wherein a passage aperture is located facing the second open end of the connecting tip.

9. The injection assembly according to claim 1, wherein the injecting element is connected to the supporting portion via at least one breakable area.

10. The injection assembly according to claim 1, wherein the coupling portion is configured to cooperate with the obturator so that a rotation of the coupling portion about an axis of rotation parallel to a direction of extension of the coupling part drives in rotation the obturator so as to cause a rupture of the breakable area.

11. The injection assembly according to claim 1, wherein the coupling tip of the injection device of a Luer or Luer Lock type.

12. An injection assembly, including:
a prefilled injection device comprising a coupling tip, the coupling tip including a tubular coupling part intended for a passage of a fluid and a threaded locking sleeve surrounding the tubular coupling part,
an obturator obturating a free end of the tubular coupling part of the coupling tip, the obturator being connected by a breakable area to the free end of the tubular coupling part, and
a protection device comprising:
a one-piece body including:
a protective portion removably mounted on the coupling tip of the injection device so as to cover and protect at least partially said coupling tip, the protective portion including a skirt engaged on an outer wall of the threaded locking sleeve of the coupling tip,
a coupling portion connected to the protective portion and configured to cooperate with the obturator, and
a supporting portion connected to the coupling portion, and
an injecting element removably mounted on the supporting portion in a storage position, the injecting element comprising an injection needle and a connecting tip fluidly connected to the injection needle, the connecting tip being adapted to be mounted on the coupling tip of the injection device in a position of use of the injecting element, the injecting element and the supporting portion being arranged in such a way that, in the storage position of the injecting element, the connecting tip is accessible to cooperate with the coupling tip.

* * * * *